United States Patent [19]

Huerta

[11] Patent Number: 5,501,215

[45] Date of Patent: Mar. 26, 1996

[54] VENTILATION TUBE WITH EVACUATION SHEATH

[76] Inventor: Christine M. Huerta, 775 28th Ave., North, St. Petersburg, Fla. 33704

[21] Appl. No.: 442,484

[22] Filed: May 16, 1995

[51] Int. Cl.$^6$ .................................................. A61M 16/00
[52] U.S. Cl. .................................. 128/207.15; 128/207.17
[58] Field of Search ...................... 128/200.26, 207.14, 128/207.15, 207.17, 207.16; 604/97, 98, 103

[56] References Cited

U.S. PATENT DOCUMENTS

| | | | |
|---|---|---|---|
| 3,544,668 | 12/1970 | Dereniuk | 604/103 |
| 3,734,100 | 5/1973 | Walker et al. | 604/103 |
| 4,231,365 | 11/1980 | Scarberry | 128/207.15 |
| 4,305,392 | 12/1981 | Chester | 128/207.15 |
| 4,327,721 | 5/1982 | Goldin et al. | 128/207.15 |
| 4,334,534 | 6/1982 | Ozaki | 128/207.15 |
| 4,584,998 | 4/1986 | McGrail | 128/207.15 |
| 4,607,635 | 8/1986 | Heyden | 128/207.15 |
| 4,693,243 | 9/1987 | Buras | 128/207.15 |
| 4,762,125 | 8/1988 | Leiman et al. | 128/207.15 |
| 4,955,375 | 9/1990 | Martinez | 128/207.15 |
| 4,976,261 | 12/1990 | Gluck et al. | 128/207.14 |
| 5,065,755 | 11/1991 | Klaffa | 128/207.15 |
| 5,065,757 | 11/1991 | Dragisic et al. | 128/207.15 |
| 5,067,497 | 11/1991 | Greear et al. | 128/207.15 |
| 5,143,062 | 9/1992 | Peckham | 128/207.15 |
| 5,146,916 | 9/1992 | Catalani | 128/207.15 |
| 5,311,864 | 5/1994 | Huerta | 128/207.15 |

Primary Examiner—Edgar S. Burr
Assistant Examiner—Eric P. Raciti
Attorney, Agent, or Firm—Charles E. Lykes, Jr.

[57] ABSTRACT

An improved breathing assistance ventilation tube for assisting a patient suffering from pulmonary distress and which includes a balloon cuff and evacuation means for evacuating undesired fluids from a patient's tracheal region. The invention teaches an improved evacuation apparatus and improved means for fastening anf linking the evacuation and balloon cuff means to either each other or to the ventilation tube or both.

20 Claims, 2 Drawing Sheets

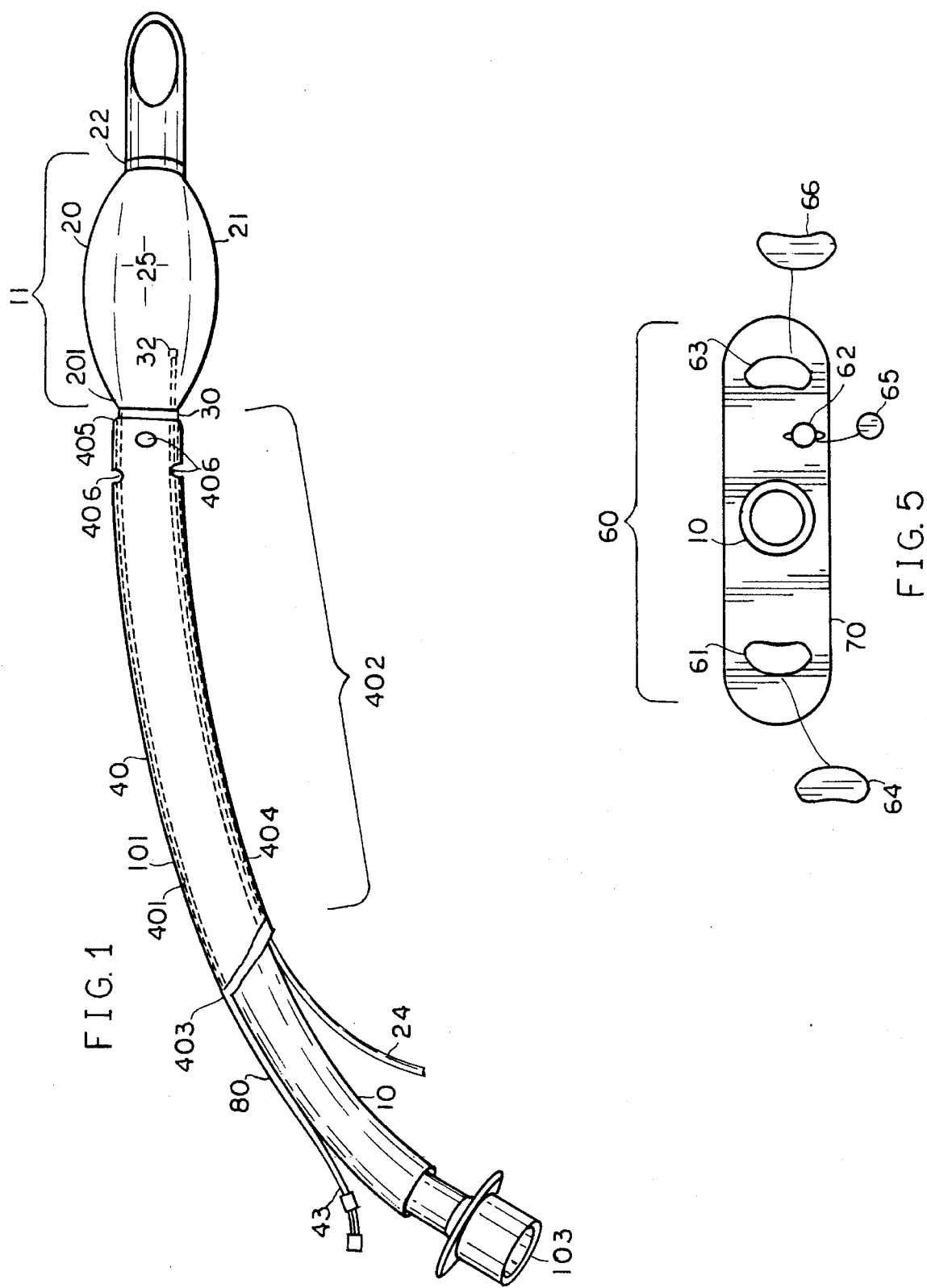

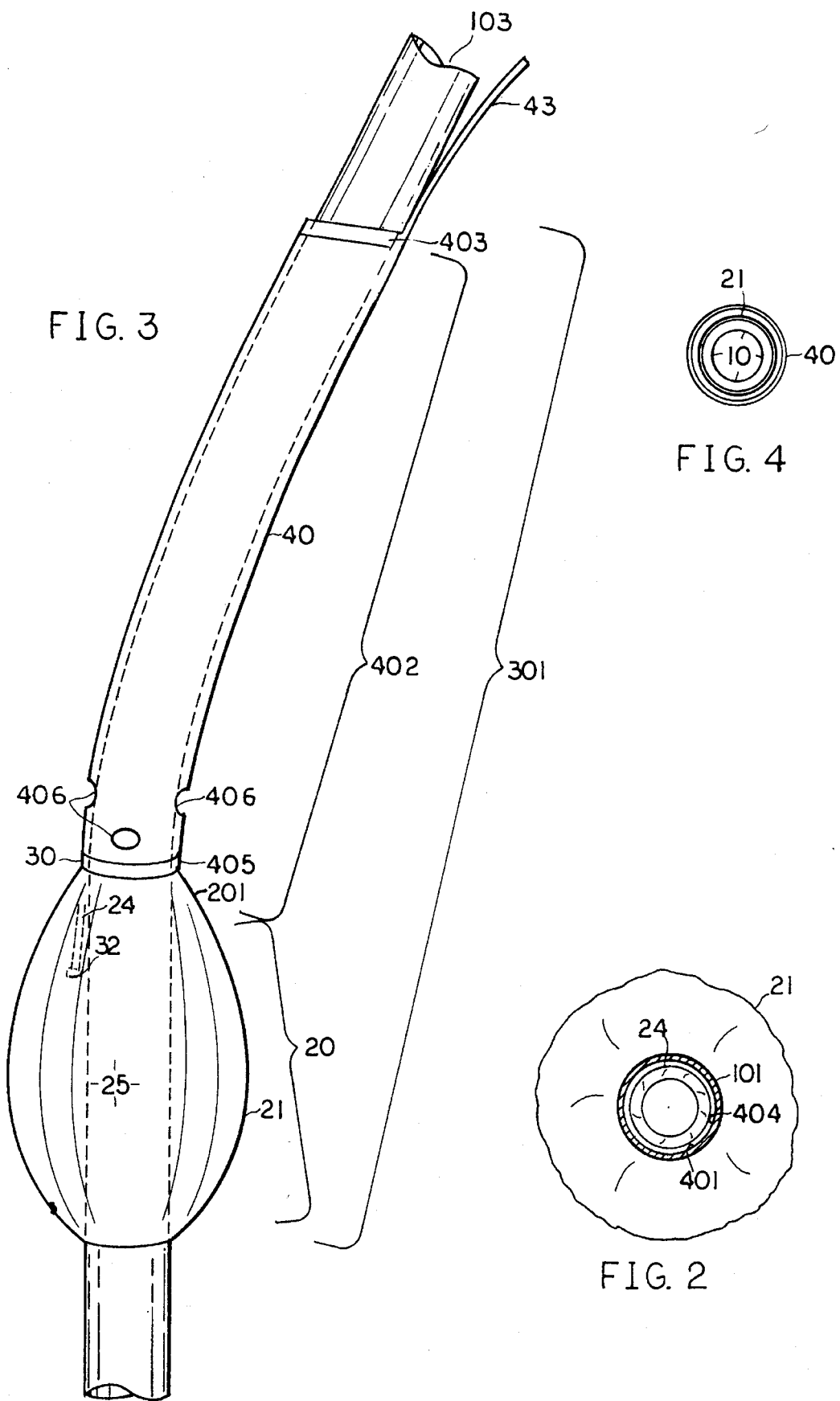

VENTILATION TUBE WITH EVACUATION SHEATH

FIELD OF THE INVENTION

The invention relates to tracheal and endotracheal tubes, particularly those which are adapted with means to block the air passage during ventilation operations and to assist in dispensing medication and evacuation undesired fluids. The Inventor has previously developed a ventilation tube with a sheath and such has been patented as U.S. Pat. No. 5,311,864, issued May 17, 1994. All of the specification and description of the prior invention should be considered incorporated herein by this reference.

BACKGROUND OF THE INVENTION

Previously the Inventor has developed a ventilation tube which incorporated the use of a sheath around the ventilation tube above the balloon cuff to assist in the function of evacuating undesired fluids from a person's throat which may pool in the regions surrounding the balloon cuff.

The previous invention comprised an unsealed sheath which surrounded the ventilation tube. The sheath assisted in providing space for various lumens to be disposed and provided a space in which fluids could pool in the general region of the balloon cuff.

The earlier invention also teaches the use of a semi-rigid radial member (which was referenced as a rigid collar member) in the general region of the balloon cuff to provide both physical protection to the balloon cuff as well as to assist in the blockage and pooling of fluids.

It may be useful to develop such an apparatus with all of the features of the previous invention, but which does not require the use of a rigid or semi-rigid balloon cuff upper end. It is also helpful to devise a means of providing even better suction than is presently available. In particular, it would be useful to insure that suction pressure may be delivered all around the circumference of the ventilation tube.

SUMMARY OF THE INVENTION

The Inventor has developed an improved version of her earlier ventilation tube and sheath apparatus. The Inventor has further adapted this basic idea in a manner designed to improve the evacuation function. Whereas previously the sheath housed lumens and traveled along the length of the ventilation tube and fit loosely around the ventilation tube, the Inventor has adapted a new apparatus in which a sealed sheath portion surrounds a portion of the ventilation tube. By sealing the upper end of the sheath, it is possible to deliver suction pressure throughout the length and all about the circumference of the ventilation tube, specifically at the region near the balloon cuff. This enables more effective suction.

The inventor has solved the problems remaining from the prior art with an apparatus which facilitates the gathering of undesired fluids from all around the ventilation tube as well as points all around the tracheal region above the balloon cuff. The present invention additionally facilitates the safe and efficient evacuation of those fluids with no possibility of interference of or by the operation of the balloon cuff. An alternative embodiment of the apparatus includes a tracheal plate to seal a tracheal incision and to facilitate fluid communication between the various suction and ventilation sources and their respective evacuation and ventilation areas.

The invention generally comprises a ventilation tube with surrounding balloon cuff. A concentric evacuation tube surrounds the ventilation tube from immediately above the cuff, at the common joining band, to a point superior to the ports in the evacuation tube. At this point, the evacuation tube extends over to only one side of the ventilation tube, becoming the evacuation sheath. The ventilation tube and evacuation sheath will be attached serving as a single unit initially, to allow easy insertion. The proximal end of the evacuation sheath will be able to peel away from the ventilation tube; to a certain point, and at the same time be stable enough to maintain its own shape. This process will allow the ventilation tube to be cut at any time it is required without altering the function of the evacuation sheath. The proximal end of the evacuation sheath will have an access port to allow communication of pressure and fluids. This port may be adapted with a cap or cover for times the evacuation sheath is not in use the opening would be sealed.

A lumen for inflating and deflating the balloon cuff may be passed through either the evacuation tube or ventilation tube into the balloon cuff without ever opening in the evacuation tube area. For tracheal incision insertion, evacuation lumens are passed through a plate which rests snugly against and seals the tracheal incision. The length of the concentric evacuation tube must be the same size or longer than the distance from the cuff to the tracheal incision.

The concentric sheath evacuation region may be adapted with a series of ports about its exterior surface just proximal from the cuff. Undesired fluids will be efficiently pooled, isolated and may be collected from the ports in the evacuation tubes. All of these fluids can be safely and efficiently evacuated through the evacuation lumen.

It is, then an object of the present invention to provide a more efficient and safe endotracheal or tracheostomy ventilation and evacuation apparatus.

It is a further object of the present invention to provide such an apparatus with the capability of isolating undesired fluids from all around the ventilation tube for efficient evacuation.

It is a further object of the present invention to provide such an apparatus with no possibility of interference between the balloon cuff and evacuation functions.

It is a further object of the present invention to provide means for safe and efficient use of such ventilation and evacuation device in conjunction with a tracheal incision.

It is further object of the present invention to provide such functions and also provide a means for introducing fluids to the trachea through the evacuation tube chamber of a endotracheal or tracheostomy device.

Other features and advantages of the present invention will be apparent from the following description in which the preferred embodiments have been set forth in conjunction with the accompanying drawings.

BRIEF DESCRIPTION OF THE DRAWINGS

In describing the preferred embodiments of the invention reference will be made to the series of figures and drawings briefly described below.

FIG. 1 depicts a side view of the overall apparatus permitting viewing of the balloon cuff, ventilation and evacuation tubes, and evacuation and cuff lumens.

FIG. 2 depicts a cross-section view of the apparatus at the proximal side of the balloon cuff permitting viewing of the common joining band, balloon cuff, and cross sectional views of ventilation and evacuation tubes and evacuation and cuff lumens.

FIG. 3 is a closeup oblique depiction of the apparatus in the region of the proximal side of the balloon cuff depicting the relationship between balloon cuff, common joining band, evacuation tube, and ventilation tube and operation of the evacuation and cuff lumens.

FIG. 4 depicts a cross-section of one possible configuration of a common joining band.

FIG. 5 depicts the basic apparatus adapted with a plate for use of the basic apparatus within and through a tracheal incision.

Apparatus and means may be described herein which are not depicted by the accompanying drawings. Such means and apparatus, if described, should be considered part of the specification even if not so depicted by a figure or drawing.

DETAILED DESCRIPTION OF THE PREFERRED AND ALTERNATE EMBODIMENTS

Reference will now be made in detail to the present preferred embodiments of the invention, examples of which are illustrated in the accompanying drawings. While the invention will be described in connection with its preferred embodiments, it will be understood that it is not intended to limit the invention to those embodiments. On the contrary, it is intended to cover all alternatives, modifications, and equivalents as may be included within the spirit and scope of the invention defined in the appending claims.

Making reference first to FIG. 1, the major components of the apparatus are identified. A ventilation tube (10) runs throughout a length sufficient to pass through a patient's mouth or nose and into the lung opening (neither of which are depicted). A balloon cuff (20) is placed about the ventilation tube (10) at a position (11) so that it will be between the patient's epiglottis (not depicted) and lung opening (not depicted). The membrane (21) of the balloon cuff (20) is radially connected to the ventilation tube (10) at its distal (away from the mouth) end (22). At its proximal end (23), the balloon cuff membrane (21) is radially connected to a joining band (50) which is common to both the balloon cuff and an evacuation sheath (40). This common joining band (30) is a point where the proximal end (21) of the balloon cuff (20) is connected with the ventilation tube (30) by means of a band (22) making sealed contact with the ventilation tube (10) within the region of the common joining band (30).

Concentrically about the ventilation tube (10) and extending proximally from the common joining band (30) is provided an evacuation sheath (40), which may also be described as a concentric tube to the ventilation tube (10). The space between the outer surface (101) of the ventilation tube (10) and the inner surface (401) of the evacuation sheath is slight, but the evacuation sheath (40) is to be constructed of a material and in a manner to maintain some separation along the length (402) of the evacuation sheath (40) from the common joining band (30) proximally to a point (403) where the evacuation sheath (40) is sealed concentrically about the ventilation tube (10).

This point of sealing must be a band (403) about the ventilation tube (10), but can be oriented diagonally and need not be regular so long as it closes off the proximal end of the evacuation sheath region (404) between the evacuation sheath (40) and ventilation tube (10). This is to permit the application of negative pressure (suction) through a port at its proximal end and throughout the space between the ventilation tube and evacuation sheath throughout the area between the common joining band and the proximal sealed evacuation sheath and ventilation tube connection.

The evacuation sheath (40) must form such an evacuation region (404) sufficient to permit the flow of fluid (30) about and down the length of the ventilation tube (10) to pool at the distal end (405) of the evacuation sheath (40) just proximal from the common joining band. The evacuation tube (40) may also be adapted with a series of ports (406) at points about its circumference near the common joining band (30). These ports (406) would be of adequate dimension to permit fluids to enter the evacuation sheath (40) from the surrounding region, particularly at the common joining band (30) and at the proximal end (201) of the balloon cuff (20).

At a point proximal to the sealed connection between the evacuation sheath and the ventilation tube is provided an accessory sheath (80), which may be manipulated away (peeled) from the ventilation tube to permit adjustment and positioning of the various pressure and evacuation lumens, but retain its structural integrity and return to a position next to the ventilation tube. This accessory sheath must be of adequate length to pass from the evacuation tube back up through the tracheal region and then out of the patient through either the patient's mouth or an incision in the tracheal region (areas are not depicted) (30).

The accessory sheath (40), at a point outside the patient's body, may be gathered into a lumen or access port (not depicted in FIG. 1) which permits pressure communication throughout the evacuation sheath (40). Such a lumen or access port (43) could also be used (with positive pressure) to deliver medication to the distal ports.

The balloon cuff lumen (24) distally terminates into a port (32) in the balloon cuff interior (25). The proximal end (not depicted) of the balloon cuff lumen (24) may be in communication with alternating sources of positive and negative pressure to facilitate inflating and deflating the space between the balloon cuff membrane (21) and the ventilation tube (10).

Some comment should be made about the proximal end of the ventilation tube (10). In the case of an endotracheal device, the distal end (102) of the ventilation tube (10) is long enough to pass through the mouth or nose of the patient allowing a balloon cuff (20) to be positioned between the epiglottis and lung. This configuration is depicted in FIG. 1. A pressure ventilation means (not depicted) at this proximal end (103) may be used to ventilate the patient's lungs (not depicted). Additionally, the balloon cuff lumen (24) and evacuation sheath lumen (43) are each of adequate length to be passed out through the patient's mouth or nose from these positions. Pressure devices connected thereto can be used to perform the functions of balloon inflation and deflation and suction of the undesired fluids.

FIG. 2 depicts a cross section of the ventilation tube (10) and evacuation sheath (40) at a point between the common joining band (30) and the sealed connection (403) between the ventilation tube (10) and evacuation sheath (40). It should be noted that a lumen (24) for applying the positive and negative pressure to the balloon cuff may be passed through the width (105) of the ventilation tube wall (106). However, such balloon cuff lumen (24) could also be passed through the space between the evacuation sheath and ventilation tube or within the ventilation tube (10) itself. All that is necessary is that a means of delivering unobstructed positive and negative pressure as desired from a point outside the patient's body to a point within the balloon cuff be supplied.

FIG. 3 depicts a close up view of the region (301) about the common joining band (31) depicting the distal end (406) of the evacuation sheath (40), the proximal end (202) of the balloon cuff (20), and the ports at the distal end of the evacuation sheath. The common joining band (30) may be very narrow and very thin. What is important is that some small separation between the evacuation ports and the balloon cuff membrane (21) be maintained. This will permit fluids which may have gathered at the proximal end (201) of the balloon cuff (20) to be evacuated without harm to or interference from the balloon cuff membrane (21).

The common joining band (30) could be made by concentrically layering one or more layers of balloon cuff membrane (21) and a layer of evacuation sheath (40) against the ventilation tube (10). This would create a separation between the ventilation tube (10) and the evacuation sheath (40). Such a configuration is depicted in FIG. 4. The common joining band (30) can, in reality, be affixed to the ventilation tube, and/or the proximal end of the balloon cuff, and/or the evacuation sheath by any means with which plastics may be fixed to one another. These means may include the use of adhesives, heat fusion, or pressure friction, as long as the common joining band (30) and balloon cuff (20) are permanently positioned along the ventilation tube (10) so that they will remain in position.

Making reference now to FIG. 5, an alternative embodiment of the present invention is described. Such alternative embodiment incorporates the art taught in the preferred embodiment and is in keeping within the spirit and scope of the present invention relating to such a device for use with tracheal incision.

There are occasions when it is necessary to perform the breathing augmentation function from an incision through the tracheas. This may be the result of trauma or blockage. This is commonly done by making an incision into the tracheal region through the neck which is large enough to pass the various lumens and tubes. Such incisions are typically made below the larynx.

It can be seen that this presents an additional exposure to the risk of infection. Secretions build up on top of the cuff and leak out of the surgical incision onto the patient's chest, creating a medium for infection to the surgical site. In order to control this risk as well as to facilitate the utility of the breathing assistance components as described above, the inventor has developed a plate (60) which may be used to cover the incision and maintain an appropriate position and spatial relationship between the various tubes and lumens. Such a plate (60) is depicted in FIG. 4. It can be seen that the plate (60) is designed to generally fit the curvature of the neck and to cover the tracheal incision (70).

Whereas present plates are shaped with a curvature below the ventilation tube (presumably in order to nestle with the clavicle wedge) the present plate is seen as a straight band. Eliminating the curvature avoids potential aggravation of the swollen area about the incision. Through the plate are openings (61, 62, 63) which correspond with the diameters of the ventilation tube (10, 61) and the balloon cuff (24, 62) and evacuation lumen or access port (43, 63). Rather than pass the proximal ends of these channels through the mouth, they can be passed out through the openings (61, 62, 63) in the plate, which also serve to stabilize and help identify and distinguish them from each other.

A primary advantage of this plate (60) is that it may cover tracheal incision. By providing these ports (61, 62, 63) for each of the tubes and lumens required to operate the device, it is unnecessary to make any further entries in the tracheal region. The incision can be dressed, healed and covered leaving sufficient apparatus available to ventilate, operate the cuff, evacuate the fluids, and, as may be necessary apply medications to the patient's tracheal region. A primary advantage of this plate (60) as adapted with the evacuation lumen port (63) is that it permits the evacuation of the fluids through and away from the plate (10). Formerly these evacuation means could not be applied through a tracheal incision.

The ports (61, 62, 63) may be adapted with caps or covers (64, 65, 66) so that the plate (60) may be left in position but the openings (61, 62, 63) sealed. This would permit rapid and easy reactivation of breathing augmentation as may be necessary with a given patient without making a new tracheal incision.

A secondary benefit of this is in the emotional well being of the patient. Patients who undergo tracheal incisions are typically left with an unsightly wound and dressing in their tracheal region. The wound itself requires frequent attention secondary to the secretions spilling/leaking out and on to the patient's chest. With the apparatus adapted with this plate, these drawbacks are avoided. A patient with such an apparatus is more likely to feel comfortable in the presence of family and friends and is less apt to experience discomfort from the need to insert and remove tubes or to have unsecured tubes protruding from the tracheal region.

In order to prevent the inadvertent confusion between ports, the evacuation port (61) and balloon cuff port (62) could be made of different sizes or different means of attachment, or both. This would prevent the patient or attendant from erroneously applying inappropriate pressure or medication, or from otherwise confusing functions. Additionally, while this embodiment has been described with the various lumens and ports terminating at the plate, there is no reason that the lumens and tubes could not be extended through the plate for attachment to any desired source of pressure.

Among the many advantages of this device is the elimination of direct contact with potentially harmful fluids by either the patient or treating personnel. This is because the fluids are evacuated from the target region directly through the evacuation apparatus.

Reference has been made to various sources of vacuum pressure. Such pressure sources are well known in the state of the art and not separately claimed here. It is, however, worth mentioning that, as adapted with the evacuation sheath, the device as presently taught may be safely operated with either a machine vacuum (at pressures up to −200 cm of water pressure) or manually through a syringe. This makes the device useful either in a hospital or in the course of home care.

Further modification and variation can be made to the disclosed embodiments without departing from the subject and spirit of the invention as defined in the following claims. Such modifications and variations, as included within the scope of these claims, are meant to be considered part of the invention as described.

Having now described the present invention, the invention is claimed with respect to its preferred embodiments. Such claims are intended to incorporate and include the elements of the invention which distinguish it from the prior art and achieve improvement over the prior art and are not intended to be limited by elements not necessary to establish such distinction and improvement.

What is claimed is:

1. A breathing augmentation apparatus for insertion from a point outside a patient's body through the patient's tracheal region to a patient's lung cavity, the apparatus comprising;

a ventilation tube, said ventilation tube being of a flexible material and of diameter adequate to pass sufficient air or oxygen at a pressure safe to a person's lung but small enough to fit through said tracheal region without trauma or damage to the epiglottis or interior throat surfaces and of sufficient length to reach from a point outside a patient's body, through said tracheal region and to the lung cavity opening;

a balloon cuff having a membrane, said balloon cuff being positioned radially about a ventilation tube at a point between said patient's epiglottis and lung opening, said balloon cuff further being adapted to alternatively be inflated to permit its expansion radially about said ventilation tube to fill the space between said ventilation tube and a patient's throat wall and then be deflated to permit its collapse upon said ventilation tube, said balloon cuff further being adapted, at its point along said ventilation tube most proximal to the exit of said ventilation tube from a patient, with a common joining band, said common joining band being further adapted to radially surround from said ventilation tube and hold said balloon cuff in place and to permit the insertion of a fluid pressure lumen for inflating and deflating said balloon cuff from a pressure source outside a patient's body;

an evacuation sheath having proximal and distal ends, said evacuation sheath further comprising a concentric sheath about said ventilation tube and extending from said common joining band proximally to a sealed connection about said ventilation tube through which a pressure source from outside a patient's body may be delivered to the space defined between said ventilation tube and said evacuation sheath, said evacuation sheath being adapted with one or more ports about its circumference near said common joining band.

2. The invention described in claim 1 in which said common joining band is of a width to provide an adequate separation between said evacuation sheath and said balloon cuff to prevent said balloon cuff membrane from interfering in the suction of fluids pooled proximally from said balloon cuff membrane and about said common joining band and to protect said balloon cuff membrane from being damaged or distorted from said evacuation pressure.

3. The invention described in claim 1 in which said balloon cuff lumen travels through the wall of said ventilation tube.

4. The invention described in claim 1 in which said balloon cuff lumen is positioned along the ventilation tube and within said common joining band from a point within said balloon cuff, through said common joining band, through said evacuation sheath, through said sealed connection, and outside a patient's body.

5. A breathing augmentation apparatus for insertion from a point outside a patient's body through a patient's tracheal region to a patient's lung cavity, the apparatus comprising;

a ventilation tube, said ventilation tube being of a flexible material and of diameter adequate to pass sufficient air or oxygen at a pressure safe to a person's lung but small enough to fit through said tracheal region without trauma or damage to a patient's epiglottis or interior throat surfaces and of sufficient length to reach from a point outside a patient's body, through a patient's tracheal region and to a patient's lung cavity opening;

a balloon cuff having a membrane, said balloon cuff being positioned radially about said ventilation tube at a point between a patient's epiglottis and lung opening, said balloon cuff further being adapted to alternatively be inflated to permit its expansion radially about said ventilation tube to fill the space between said ventilation tube and a patient's throat wall and then be deflated to permit its collapse upon said ventilation tube, said balloon cuff further being adapted, at its point along said ventilation tube most proximal to the exit of said ventilation tube from said patient, with a common joining band, said common joining band being further adapted to radially surround from said ventilation tube and hold said balloon cuff in place and to permit the insertion of a fluid pressure lumen for inflating and deflating said balloon cuff from a pressure source outside a patient's body;

an evacuation space, said evacuation space further comprising the space between said ventilation tube and a concentric evacuation sheath having proximal and distal ends about said ventilation tube and extending from said common joining band proximally and about said ventilation tube to a pressure source outside a patient's body, said fluid collection region being further adapted with one or more ports about its circumference near said common joining band; and a tracheal plate, said tracheal plate being provided with ports for receiving the proximal ends of said evacuation sheath, ventilation tube, and balloon cuff lumens, said tracheal plate being further adapted to cover a tracheal incision.

6. The invention described in claim 5 in which said balloon cuff lumen is positioned along the ventilation tube and within said fluid collection region from a point within said balloon cuff common joining band, through said common joining band, and outside a patient's body.

7. The invention described in claim 1 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

8. The invention described in claim 2 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

9. The invention described in claim 3 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

10. The invention described in claim 4 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

11. The invention described in claim 5 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

12. The invention described in claim 6 in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

13. The invention described in claim 1 in which said common joining band further comprises one or more pleated layers of said balloon cuff membrane which are further concentrically layered upon said ventilation tube and upon which one or more pleated layers of evacuation sheath are further concentrically layered upon said balloon cuff membrane layers so as to form a fluid tight seal within both the balloon cuff and evacuation sheath region.

14. The invention described in claim 1 in which said common joining band further comprises one or more layers of said balloon cuff membrane which are further concentrically layered upon said ventilation tube and which are fused to said ventilation tube by heat in order to form a fluid tight seal between said balloon cuff membrane and said ventilation tube.

15. The invention described in claim 1 in which said common joining band further comprises one or more layers of said balloon cuff membrane which are further concentrically layered upon said ventilation tube and which are fastened to said ventilation tube by use of an adhesive in order to form a fluid tight seal within both the balloon cuff and evacuation sheath region.

16. The invention described in claim 1 in which said common joining band further comprises one or more layers of said evacuation sheath which are further concentrically layered upon said ventilation tube and which are fused to said ventilation tube by heat in order to form a fluid tight seal between said evacuation sheath and said ventilation tube.

17. The invention described in claim 1 in which said common joining band further comprises one or more layers of said evacuation sheath which are further concentrically layered upon said ventilation tube and which are fastened to said ventilation tube by use of an adhesive in order to form a fluid tight seal within both the balloon cuff and evacuation sheath region.

18. The invention described in claim 1 in which said common joining band further comprises one or more layers of said balloon cuff membrane which are further concentrically layered upon said ventilation tube and upon which one or more layers of evacuation sheath are further concentrically layered upon said balloon cuff membrane layers so as to form a fluid tight seal within both the balloon cuff and evacuation sheath region and in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

19. The invention described in claim 1 in which said common joining band further comprises one or more layers of said balloon cuff membrane which are further concentrically layered upon said ventilation tube and which are fastened to said ventilation tube in order to form a fluid tight seal between said balloon cuff membrane and said ventilation tube and in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

20. The invention described in claim 1 in which said common joining band further comprises one or more layers of said evacuation sheath which are further concentrically layered upon said ventilation tube and which are fastened to said ventilation tube in order to form a fluid tight seal between said evacuation sheath and said ventilation tube and in which an evacuation lumen is placed within an accessory sheath and placed in fluid communication with said evacuation sheath in a means to permit common fluid pressure communication between said evacuation sheath and said evacuation pressure;

said accessory sheath further comprising a releasable sheath about said ventilation tube beginning at or near the proximal end of said evacuation sheath and extending proximally along said ventilation tube and which is further adapted to be peeled away from said ventilation tube to allow manipulation of said evacuation lumen and then placed back into place about said ventilation tube.

* * * * *